(12) United States Patent
Qin (10) Patent No.: US 12,186,063 B2
(45) Date of Patent: Jan. 7, 2025

(54) MEASUREMENT OF BLOOD VOLUME USING FOURIER-TRANSFORM BASED VELOCITY-SELECTIVE PULSE TRAINS ON MRI

(71) Applicant: THE JOHNS HOPKINS UNIVERSITY, Baltimore, MD (US)

(72) Inventor: Qin Qin, Ellicott City, MD (US)

(73) Assignee: The Johns Hopkins University, Baltimore, MD (US)

( * ) Notice: Subject to any disclaimer, the term of this patent is extended or adjusted under 35 U.S.C. 154(b) by 102 days.

(21) Appl. No.: 17/161,420

(22) Filed: Jan. 28, 2021

(65) Prior Publication Data

US 2021/0228096 A1 Jul. 29, 2021

Related U.S. Application Data (60) Provisional application No. 62/966,648, filed on Jan. 28, 2020.

(51) Int. Cl.
| | | |
|---|---|---|
| *A61B 5/029* | (2006.01) | |
| *A61B 5/00* | (2006.01) | |
| *A61B 5/055* | (2006.01) | |
| *G01R 33/44* | (2006.01) | |
| *G01R 33/50* | (2006.01) | |

(Continued)

(52) U.S. Cl.
CPC .............. *A61B 5/029* (2013.01); *A61B 5/055* (2013.01); *A61B 5/7257* (2013.01); *G01R 33/448* (2013.01); *G01R 33/50* (2013.01); *G01R 33/5618* (2013.01); *G01R 33/56518* (2013.01)

(58) Field of Classification Search
CPC ........ A61B 5/029; A61B 5/055; A61B 5/7257; G01R 33/448; G01R 33/50; G01R 33/5618; G01R 33/56518
See application file for complete search history.

(56) References Cited

U.S. PATENT DOCUMENTS

| | | | |
|---|---|---|---|
| 6,252,399 B1 * | 6/2001 | Pruessmann | G01R 33/446 324/307 |
| 2010/0030062 A1 * | 2/2010 | Bolar | A61B 5/055 600/419 |

(Continued)

OTHER PUBLICATIONS

Wu, W., et al., "Intravascular effect in velocity-selective arterial spin labeling: The choice of inflow time and cutoff velocity," NeuroImage. Vol 32, 2006. p. 122-128 (Year: 2006).*

*Primary Examiner* — Sean A Frith (57) ABSTRACT

The present invention is directed to a system and method for determining blood volume in a subject. Blood volume is an important hemodynamic parameter for monitoring many disorders, such as stoke and cancer. Current MRI techniques for quantification of absolute blood volume for such clinical applications all require injecting exogenous contrast agents. To reduce associated safety risks and cost, the present invention is directed to a non-contrast-enhanced MRI method for blood volume mapping on MRI. The technique of the present invention employs velocity-selective (VS) pulse trains in paired control and label modules for separating vascular signal by subtraction. The Fourier-transform based VS saturation pulse train (FT-VSS) of the present invention has improved performance over conventional VS pulse trains for the blood volume measurement.

20 Claims, 7 Drawing Sheets

(51) Int. Cl.
  *G01R 33/561* (2006.01)
  *G01R 33/565* (2006.01)

(56) References Cited

U.S. PATENT DOCUMENTS

| | | | |
|---|---|---|---|
| 2016/0358328 A1* | 12/2016 | Falahatpisheh | G16H 50/50 |
| 2017/0176564 A1* | 6/2017 | Qin | G01R 33/56563 |
| 2017/0293008 A1* | 10/2017 | Qin | G01R 33/50 |

* cited by examiner

MEASUREMENT OF BLOOD VOLUME USING FOURIER-TRANSFORM BASED VELOCITY-SELECTIVE PULSE TRAINS ON MRI

CROSS REFERENCE TO RELATED APPLICATIONS

This application claims the benefit of U.S. Provisional Patent Application No. 62/966,648 filed Jan. 28, 2020, which is incorporated by reference herein, in its entirety.

GOVERNMENT SUPPORT

This invention was made with government support under grant number K25 HL121192 and P41 EB015909 awarded by the National Institutes of Health. The government has certain rights in the invention.

FIELD OF THE INVENTION

The present invention relates generally to medical imaging. More particularly, the present invention relates to a system and method for measurement of blood volume using MRI.

BACKGROUND OF THE INVENTION

The ability to estimate cerebral blood flow (CBF) and cerebral blood volume (CBV) quantitatively without relying on exogenous contrast agents provides a non-invasive and often preferred alternative to dynamic susceptibility contrast perfusion weighted imaging (DSC-PWI), particularly when there is contraindication to Gadolinium based contrast agent, hypersensitivity reaction, risk of nephrogenic systemic fibrosis (3) and nowadays the growing concern (even though with unknown health effects) of Gadolinium deposition in tissues after repeated contrast administration.

Arterial spin labeling (ASL) methods typically apply spatially selective labeling modules on the supplying arteries proximal to the imaging volumes for assessment of cerebral blood flow (CBF) or arterial CBV ($CBV_a$). However, spatially selective ASL is limited by the transit time of the labeled spins to various vascular compartments in the imaging volume. CBF and CBV measurements are affected by prolonged transit time caused by conditions such as arterial steno-occlusive cerebrovascular diseases.

To reduce the sensitivity to transit time, velocity-selective (VS) labeling modules, which embed flow-sensitive gradients within spatially non-selective $90°_x$-refocus-$90°_{-x}$ pulse trains, have been employed for measuring absolute CBF and recently CBV. When assuming a laminar flow distribution in vivo, the conventional VS saturation (VSS) modules dephase the magnetization of blood spins flowing above a cutoff velocity (Vc). The static tissue and the spins moving below the Vc only experience $T_2$ weighting. Correspondingly, the VS control modules negate the flow-sensitivity and exert $T_2$ weighting to all spins regardless of their velocities.

It would therefore be advantageous to provide a reliable method for measurement of blood volume using fourier-transform based velocity-selective pulse trains on MRI.

SUMMARY OF THE INVENTION

The foregoing needs are met by the present invention, which provides a method for determining blood volume for a subject including performing a Fourier-transform velocity-selective saturation (FT-VSS) pulse train with a magnetic resonance imaging scanner. The method includes embedding refocusing pulses between FT-VSS pulse trains. The method includes cancelling out a signal from static tissue. Additionally, the method includes performing a pair of acquisitions with the magnetic resonance imaging scanner. The method also includes determining blood volume from a difference signal that results from a flowing blood compartment.

The method includes generating a non-contrast-enhanced MRI map of blood volume. The method includes using FT-VSS pulse trains in paired control and label modules for separating vascular signal by subtraction. The method includes leveraging a subtraction-based method using a pair of acquisitions immediately following velocity-sensitized pulse trains for a label module and its corresponding control module, respectively. The method includes cancelling out a signal of static tissue and a resulting difference signal comes from the flowing blood compartment above a cutoff velocity. The method includes normalizing to a proton density-weighted image acquired separately and scaled with the blood T1 and T2 relaxation factors and obtaining a quantitative measurement of blood volume.

In accordance with an aspect of the present invention, a system for determining blood volume for a subject includes a magnetic resonance imager. The system also includes a non-transitory computer readable medium programmed for performing a Fourier-transform velocity-selective saturation (FT-VSS) pulse train with a magnetic resonance imaging scanner. The method includes embedding refocusing pulses between FT-VSS pulse trains. The method includes cancelling out a signal from static tissue. Additionally, the method includes performing a pair of acquisitions with the magnetic resonance imaging scanner. The method also includes determining blood volume from a difference signal that results from a flowing blood compartment.

In accordance with another aspect of the present invention, the method includes refocusing pulses comprising adiabatic pulses or composite pulses. The method includes using a velocity-sensitized labeling module comprising ±90° pulses. The method includes using velocity-encoding gradients. Additionally, the method includes leaving a gap between each gradient and RF pulse to minimize the effect of eddy currents. The method includes generating a non-contrast-enhanced MRI map of blood volume. Additionally, the method includes leveraging a subtraction-based method using a pair of acquisitions immediately following velocity-sensitized pulse trains for a label module and its corresponding control module, respectively. The method includes cancelling out a signal of static tissue and a resulting difference signal comes from the flowing blood compartment above a cutoff velocity. Further, the method includes normalizing to a proton density-weighted image acquired separately and scaled with the blood T1 and T2 relaxation factors and obtaining a quantitative measurement of blood volume.

BRIEF DESCRIPTION OF THE DRAWINGS

FIGS. 3A and 3B illustrate graphical views of simulated differences of the Mz of static spins in the presence of eddy current (EC) effects with different time constants with the Mz at EC-free conditions, at different distances to isocenter, following the 40 ms VSS in FIG. 3A and the 128 ms FT-VSS control (the first row) and label (the second row) modules in FIG. 3B.

FIGS. 4A and 4B illustrate views of errors in the signal difference caused by gradient imperfections (such as eddy currents) after employing VS control/label modules on a phantom along different orientations (L-R, A-P, S-I) of velocity-encoding gradients.

DETAILED DESCRIPTION

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains, having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

The present invention is directed to a system and method for determining blood volume in a subject. Blood volume is an important hemodynamic parameter for monitoring many disorders, such as stoke and cancer. Current MRI techniques for quantification of absolute blood volume for such clinical applications all require injecting exogenous contrast agents. To reduce associated safety risks and cost, the present invention is directed to a non-contrast-enhanced MRI method for blood volume mapping on MRI. The technique of the present invention employs velocity-selective (VS) pulse trains in paired control and label modules for separating vascular signal by subtraction. The Fourier-transform based VS saturation pulse train (FT-VSS) has improved performance over conventional VS pulse trains for the blood volume measurement.

The present invention is directed to a subtraction-based method using a pair of acquisitions immediately following velocity-sensitized pulse trains for the label module and its corresponding control module, respectively. The signal of static tissue is canceled out and the difference signal comes from the flowing blood compartment above a cutoff velocity. After normalizing to a proton density-weighted image acquired separately and scaled with the blood T1 and T2 relaxation factors, quantitative measurement of blood volume is then obtained. The FT-VSS pulse train is composed of a series of excitation pulses, interleaved with pairs of refocusing pulses and gradients. The velocity-sensitive labeling module with gradient lobes of alternating polarity yields a saturation band within the cut-off velocity. A gap between each gradient and RF pulse is kept to minimize the effect of eddy currents. The corresponding control module can either keep the all the gradients but maintain velocity-compensated waveform and balanced diffusion weighting, or have gradients turned off for a velocity-insensitive waveform. The labeling/control modules are immediately followed by acquisitions.

Advanced Fourier-transform (FT) based VS pulse trains have been developed by concatenating a series of small-flip-angle RF pulses interleaved with velocity-encoding gradients for MR angiography (MRA) and quantitative CBF mapping. In contrast to the flow-dephasing VSS pulse trains, FT-VSS labeling modules saturate static tissue while preserving spins flowing above Vc, while the control modules apply saturation universally on all spins.

Hence, FT-VSS label/control modules have concurrent capability for background suppression, which would be potentially beneficial for ASL based CBV quantification given that CBV signal comprises only a few percent of overall tissue signal and is susceptible to tissue signal fluctuations due to system instability and physiological motion.

Flow-dephasing velocity-selective saturation (VSS) pulse trains have been employed for measuring cerebral blood volume (CBV). This study is to compare the Fourier-transform based velocity-selective saturation (FT-VSS) pulse trains with the conventional VSS technique for CBV quantification. The proposed FT-VSS label and control modules were compared with conventional VSS using numerical simulations and phantom studies to evaluate their sensitivities to gradient imperfections such as eddy currents. FT-VSS and VSS prepared CBV mapping were further compared for velocity-encoding gradients along three orthogonal directions in healthy subjects at 3T. The simulations and phantom studies exhibited much reduced susceptibility to eddy currents and other gradient imperfections for the employed FT-VSS pulse trains. Compared to the VSS, FT-VSS delivered more robust CBV results and 31-50% higher temporal SNR values across the three VS encoding directions. The average CBV value obtained from FT-VSS based sequences was 5.5 mL/100 g for gray matter and 2.5 mL/100 g for white matter, comparable to literature expectations. Absolute CBV quantification employing advanced FT-VSS pulse trains were more advantageous to the existing approach using flow-dephasing VSS modules. The greater immunity to gradient imperfections and the concurrent tissue background suppression of FT-VSS pulse trains enabled more robust CBV measurements and markedly higher SNR than the conventional VSS pulse trains.

The FT-VSS pulse trains have a cutoff velocity Vc was reduced from 1.40 cm/s to 0.35 cm/s. Note that Vc here refers to a mean velocity, which is the reported value in studies measuring flowing velocities in microvasculature. For a laminar flow distribution within a vessel, the mean velocity is half of the corresponding maximum velocity in the center. In previous MRA and CBF studies, velocities were referred to as the maximum velocities in relatively large vessels of interest.

Figures 1A, 1B, 1C:
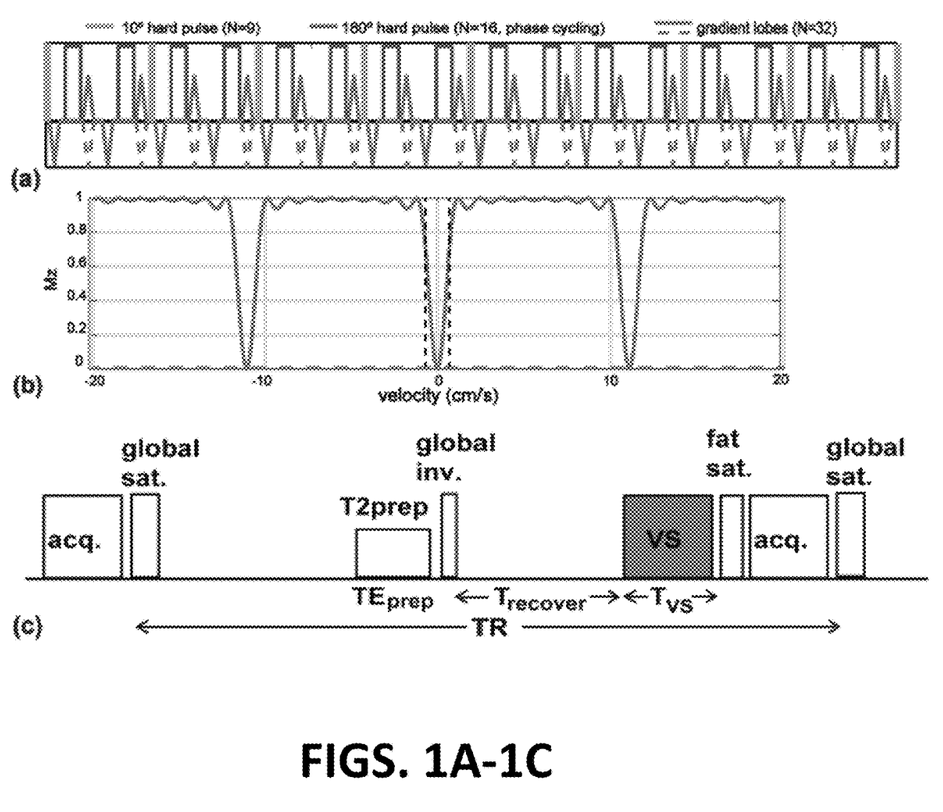
FIGS. 1A-1C illustrate graphical views of pulse sequence diagrams, according to an embodiment of the present invention.

FIGS. 1A-1C illustrate graphical views of pulse sequence diagrams, according to an embodiment of the present invention. The FT-VSS pulse train is composed of nine excitation pulses (10° hard pulses), interleaved with pairs of refocusing pulses (180° hard pulses) and gradients, that constitute eight velocity-encoding steps (16 ms each step; total duration $T_{VS}$=128 ms), as illustrated in FIG. 1A. The velocity-sensitive labeling module with triangular gradient lobes ($G_{VS}$=22 mT/m; slope: 0.6 ms) of alternating polarity yields a targeted saturation band within ±0.35 cm/s, as illustrated in FIG. 1B. The velocity-compensated control module applies unipolar gradient lobes for saturation of all the spins regardless of velocity (dashed lines in FIGS. 1A and 1B). The phase-cycling scheme for the refocusing pulses is MLEV-16, which greatly improves the immunity to B0/B1 inhomogeneity and gradient imperfections such as eddy currents.

FIG. 1A illustrates a graphical diagram of the FT-VSS pulse train with paired and phase-cycled refocusing pulses in each velocity-encoding step, gradient pairs with alternating polarity surrounding refocusing pulses for the velocity-sensitized waveform (medium grey solid lines) and unipolar gradient pairs for the velocity-compensated waveform (medium grey dashed lines for the polarity-switched gradient lobes). FIG. 1B illustrates simulated $M_z$-velocity responses of the FT-VSS pulse train (medium grey solid lines) show the preservation of spins flowing above the cutoff velocity in the passband and suppression of the static spins within the saturation band (black vertical dashed lines). The horizontal dashed lines illustrate the universal saturation response of the FT-VSS pulse train of the control module. FIG. 1C illustrates the pulse sequence diagram for CBV quantification using VS labeling and control modules, combined with a global post-acquisition saturation and $T_2$prep prepared inversion for CSF suppression.

The conventional VSS pulse train utilized in the earlier CBV study with Vc=0.35 cm/s was evaluated at the same time to compare with the performance of the new sequence. It consists of ±90° pulses enclosing double refocused hyperbolic tangent pulses with surrounding triangular gradient lobes ($G_{VS}$=26 mT/m; slope: 1.6 ms; $T_{VS}$=40 ms). Specific parameters of both VSS and FT-VSS labeling modules are listed in Table 1, below. The corresponding control modules also chose velocity-compensated gradient waveforms for a more balanced diffusion-weighting effect.

Numerical simulations using Bloch equations is based on matrix rotation were performed to compare the effect of eddy currents on the static spins at the end of the VSS and FT-VSS pulse trains using Matlab (MathWorks, Inc., Natick, Mass., USA). Responses of the longitudinal magnetizations ($M_z$) following both the label and control pulse trains with eddy current amplitude of 0.25% and time constants of $10^{-4}$–1 s were calculated for distances from −23 cm to 24 cm with intervals of 1 cm. $B_0/B_1$ inhomogeneity and $T_2$ effects were not accounted for here.

The pulse sequence for measuring CBV includes a global saturation module, a CSF-suppression module with $T_2$prep ($TE_{prep}$=300 ms) followed by a global inversion, and a VS labeling/control module immediately before a fat-suppression module and an acquisition module, as illustrated in FIG. 1C. The repetition time is set to 6.1 s with the $T_2$prep module applied at 3.5 s after the global saturation and the recovery delay $T_{recover}$ was 1.7 s. This allows the total acquisition of each CBV protocol to be within 5 min when 24 repetitions were used.

Exemplary implementations of the present invention are described herein and are included merely to provide illustration of the present invention. These examples are not meant to be considered limiting, and the present invention can be implemented in any way known to or conceivable by one of skill in the art. All the MR experiments described herein are performed on a 3T Philips Achieva scanner (Philips Medical Systems, Best, The Netherlands) using the body coil for RF transmission (maximum amplitude 13.5 µT) and a 32-channel head-only coil for signal reception. The maximum strength and slew rate for standard gradients are 40 mT/m and 200 mT/m/ms, respectively.

Phantom experiments were performed using a spherical oil phantom to evaluate the effects of gradient imperfections such as eddy currents. The sequence described above was applied without CSF nulling modules (TR=4.0 s). VS pulse trains employing both conventional VSS and FT-VSS modules were compared with the VS gradients applied along the left-right (L-R), anterior-posterior (A-P), or superior-inferior (S-I) directions, respectively. Using a 2D single-shot echo-planar imaging (EPI) acquisition for 10 consecutive axial slices, the total measurement time after 24 repetitions was about 3.4 min for each pulse train configuration. A proton density-weighted image of signal intensity ($SI_{PD}$) was also acquired with TR=10 s for normalization.

In vivo experiments were done with six healthy volunteers (range: 25-53 yrs, three males and three females). The six volunteers were instructed to keep still with their head

TABLE 1

Parameters for the labeling modules with conventional VSS and FT-VSS pulse trains used in this CBV study.

| | $T_{VS}$ (ms) | $N_{step}$ | $T_{step}$ (ms) | $T_{ref}$ (ms) | $T_G$ (ms) | $T_{ramp}$ (ms) | $G_{max}$ (mT/m) | $T_{gap}$ (ms) | Δ (ms) | $V_c$ (cm/s) | b-value (s/mm²) |
|---|---|---|---|---|---|---|---|---|---|---|---|
| VSS | 40.0 | 1 | 40.0 | 5.00 | 3.2 | 1.6 | 26.0 | 4.0 | 10.0 | 0.7 | 6.6 |
| FT-VSS | 128.0 | 8 | 16.0 | 0.87 | 1.2 | 0.6 | 22.0 | 2.2 | 8.0 | 0.7 | 1.5 |

$T_{VS}$: duration for the entire VS pulse train;
$T_{step}$: duration for each velocity encoding step;
$T_{ref}$: duration of each refocusing pulse;
$T_G$: duration of each gradient lobe;
$T_{ramp}$: ramp time for each gradient lobe;
$G_{max}$: maximum gradient strength of gradient lobes;
$T_{gap}$: the gap between the gradient and the following RF pulse;
Δ: the separation between gradient lobes of the same polarity;
$V_c$: cut-off velocity.

stabilized with foam pads. As in the phantom study, six 5-min-long CBV scans were acquired in random order using conventional VSS and FT-VSS modules each with VS gradients along three orthogonal directions. Briefly: the transverse field of view (FOV) was 186×213 mm$^2$; 10 continuous slices were acquired at 4.4 mm slice thickness; the acquisition resolution was 3.3×3.5 mm$^2$ and the reconstructed voxel size was 1.9×1.9 mm$^2$; EPI factor (the number of k-space lines collected per echo train) was 25 and sensitivity encoding (SENSE) factor was 2.5; the effective echo time (TE) was 8.7 ms. The reported specific absorption rate (SAR) percentages relative to the head averaged SAR limit of the scanner (3.2 W/kg) were comparable for VSS and FT-VSS scans (17% vs 19%). With the same resolution and acquisition scheme, a SIND image for quantification as well as a double inversion recovery (DIR) image for visualizing gray matter were acquired as in previous studies.

Experimental data were processed using Matlab. For each pulse train configuration in the phantom study, the mean and standard deviation (SD) of the subtraction errors normalized to the SIND image from all the slices were calculated as before.

Figure 2A:
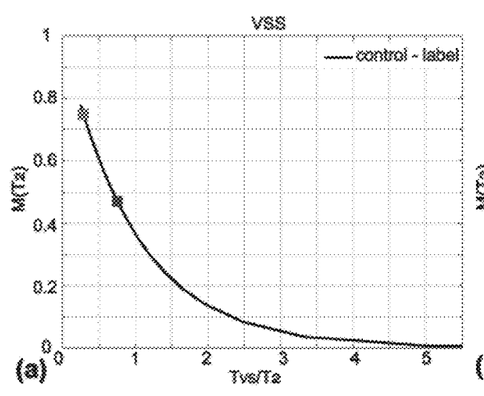
FIGS. 2A and 2B illustrate graphical views showing a comparison of the $T_2$ effects for VSS and FT-VSS pulse trains as $M_z$ of blood signal following label/control modules with various $T_{VS}/T_2$ ratios.

For in vivo studies, CBV values were computed, with specific modifications of the equations for the FT-VSS based protocols. The main difference between the VSS and FT-VSS based quantification models lies in the $T_2$ weighting of tissue and microvascular compartments during the corresponding label and control modules. For VSS modules, it is a simple $T_2$ exponential decay, $M(T_2)=\exp(-T_{VS}/T_2)$, for static tissue and flowing blood in the control scans, or static tissue and blood moving below Vc in the label scans, as illustrated in FIG. 2A. Signal for blood flowing above Vc is dephased by the VSS label modules and thus considered to be zero. For FT-VSS modules, the $T_2$ effects for label and control scans are slightly more complicated for both the passband and stopband in the label scans and nonzero for the control scans, as illustrated in FIG. 2B and described below.

Figure 2B:
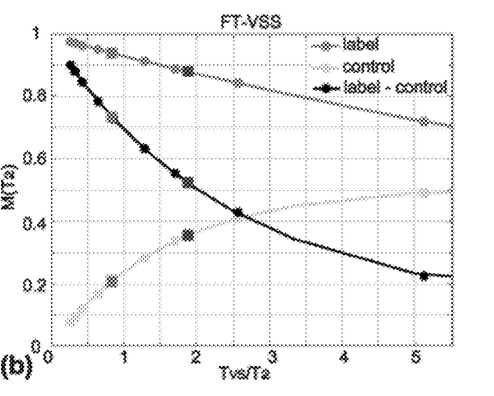

FIGS. 2A and 2B illustrate graphical views showing a comparison of the $T_2$ effects for VSS and FT-VSS pulse trains as $M_z$ of blood signal following label/control modules with various $T_{VS}/T_2$ ratios. In FIG. 2A, for VSS pulse trains, the subtraction of control and label are shown in black. In FIG. 2B, for FT-VSS label/control modules, the responses for the label modules in the passband are in medium grey; the results of the control modules are in light grey; the label and control differences are in black; the stars represent for the sampled $T_{VS}/T_2$ ratios and the lines are the fitted models. The medium grey and light grey squares in FIGS. 2A and 2B correspond to arterial and venous blood, respectively.

The signal intensity of a voxel is still described as the sum of multiple compartments with respective $T_1$ and $T_2$ weightings:

$$SI_{control}=SI_{PD}\cdot(1-x_b)\cdot M(T_{1,t})\cdot M(T_{2,t})+SI_{PD}\cdot x_b\cdot\Sigma(x_i\cdot M(T_{1,i})\cdot M(T_{2,i,control}))$$ [1]

$$SI_{label}=SI_{PD}\cdot(1-x_b)\cdot M(T_{1,t})\cdot M(T_{2,t})+SI_{PD}\cdot x_b\cdot\Sigma(x_1\cdot(1-\alpha_i)\cdot M(T_{1,i})\cdot M(T_{2,i,control})+x_i\cdot\alpha_i\cdot M(T_{1,i})\cdot M(T_{2,i,label}))$$ [2]

$$CBV=100\cdot\lambda\cdot x_b$$ [3]

The unit for CBV is mL blood/100 g tissue. $\lambda$ is the brain-blood partition coefficient, 0.9 mL blood/g tissue. $x_i$ and $\alpha_i$ are the fractions of CBV and the labeling efficiencies in arterioles ($x_a$=0.21; $\alpha_a$=0.55), capillaries ($x_c$=0.33; $\alpha_{cp}$=0), and venules ($x_v$=0.46; $\alpha_v$=0.31), based on Vc=0.35 cm/s. And the subtraction of the control and label signal intensities is:

$$SI_{label}-SI_{control}=SI_{PD}\cdot x_b\cdot\Sigma(x_i\cdot\alpha_i\cdot M(T_{1,i})\cdot(M(T_{2,i,label})-M(T_{2,i,control})))$$ [4]

Therefore, the CBV is calculated as this difference normalized by the $SI_{PD}$ image and a scaling factor related only to the $T_1$ and $T_2$ effects of the applied VS pulse trains within each microvessel compartment:

$$CBV=\frac{100\cdot\lambda\cdot(SI_{label}-SI_{control})}{SI_{PD}\cdot\sum(x_i\cdot\alpha_i\cdot M(T_{1,i})\cdot(M(T_{2,i,label})-M(T_{2,i,control})))}$$ [5]

The $T_1$ effect of the blood signal was set by the saturation recovery following the $T_{2,prep}$-inversion module:

$$M(T_{1,i})=1-\exp(T_{recover}/T_{1,i})$$ [6]

$T_{recover}$ was 1.7 s in this study. $T_{1,a}$ and $T_{1,v}$ at 3T were taken as 1.84 s and 1.70 s, respectively.

The $T_2$ effects of blood signal under the label and control modules with duration of $T_{VS}$ were characterized through Bloch equation simulations with 9 different $T_2$ values of [25, 50, 75, 100, 150, 200, 300, 400, 500] ms with the sampled $T_{VS}/T_2$ ratios as [0.26, 0.32, 0.43, 0.64, 0.85, 1.28, 1.71, 2.56, 5.12]. The averaged magnetizations in the maximal velocity range of [3.5, 7.5] cm/s were calculated as the responses for the label modules in the passband as illustrated in FIG. 2B with the medium grey stars; the magnetizations for zero velocity were taken as the results of the control modules as illustrated in FIG. 2B with the light grey stars; the label and control data were subtracted for the differences as illustrated in FIG. 2B with the black stars. These three datasets were each empirically fitted with 4-parameter models:

$$M(T_{2,i,label})-M(T_{2,i,control})=k_1+k_2\cdot k_3^{k_4\cdot T_{VS}/T_{2,i}}$$ [7]

where $[k_1, k_2, k_3, k_4]$=[0.12, 0.87, 0.72, 0.22] for label, as illustrated in FIG. 2B with the medium grey line, [0.51, −0.52, 0.24, 0.44] for control, as illustrated in FIG. 2B with the light grey line, and [0.12, 0.86, 0.34, 0.38] for the label/control difference, as illustrated in FIG. 2B with the black line, respectively. Using the relationships between $T_2$, oxygenation fraction (Y) and hematocrit fraction (Hct) established from ex vivo blood samples, $T_{2,a}$ and $T_{2,v}$ were set to be 154 ms and 68 ms for the employed 8 ms inter-echo spacing (interpolated from models with $\tau_{CPMG}$ of 5 ms and 10 ms) of the FT-VSS pulse train ($T_{VS}$=128 ms). $Y_a$=0.98, $Y_v$=0.6, Hct=0.42 were assumed for healthy adults. The $T_2$ attenuations in the label/control differences for arterial and venous blood compartments were calculated to be 0.74 and 0.52 with FT-VSS pulse trains, comparable to 0.75 and 0.47 with VSS pulse trains, as illustrated in FIGS. 2A and 2B with the light grey and dark grey squares.

Voxel-wise mean CBV maps from the repeated measures and temporal SNR maps were produced for all the scans. For each subject, a binary gray matter mask (GM) was obtained from the DIR image using an empirical threshold and a ROI within the white matter (WM) was drawn manually using the $SI_{PD}$ image. In addition, voxels with large vessels were identified through thresholding of the CBV map (>12.5 mL/100 g) acquired in the FT-VSS pulse train with VS gradients applied along the S-I direction and were excluded for the calculation. Averaged CBV and SNR values from GM and WM ROIs were calculated for each experiment.

Figure 3A:
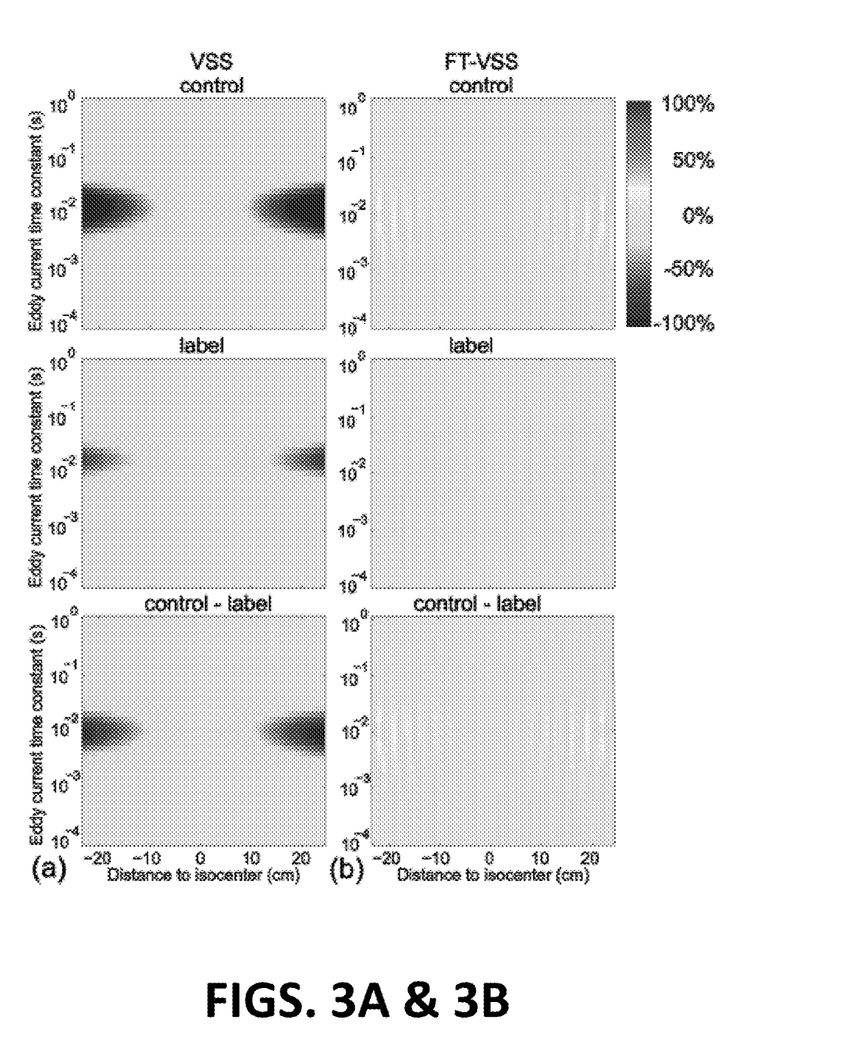

The simulated effects of eddy currents (EC) with various time constants on static spins for the 40 ms VSS and 128 ms FT-VSS modules are shown in FIGS. 3A and 3B, respectively. FIGS. 3A and 3B illustrate graphical views of simulated differences of the Mz of static spins in the presence of eddy current (EC) effects with different time constants with the Mz at EC-free conditions, at different distances to isocenter, following the 40 ms VSS in FIG. 3A and the 128 ms FT-VSS control (the first row) and label (the second row) modules in FIG. 3B. The subtraction of control and label results are displayed in the third row. The employed FT-VSS modules show much less sensitivity to EC effects. The EC sensitivities of velocity-compensated control and velocity-sensitized label modules are shown as the subtraction of tissue's Mz affected by EC from Mz targeted by each pulse train (VSS: 1; FT-VSS: 0) in the first two rows of FIGS. 3A and 3B. The label/control differences are displayed in the third row of FIGS. 3A and 3B. It is evident that the 40 ms VSS modules yielded 5 to 10 times larger EC-related errors in terms of magnitude than the 128 ms FT-VSS modules did, despite having almost twice the gradient-RF gaps (4.0 ms vs. 2.2 ms, Table 1). The range of time constants that the two pulse trains are sensitive to are 3-30 ms for VSS control, 10-30 ms for VSS label and 1-30 ms for FT-VSS label/controls, respectively. Note that for both pulse trains, EC effects are mainly off-center (>10 cm) and the majority of these effects are caused by the velocity-compensated control.

Figure 4A:
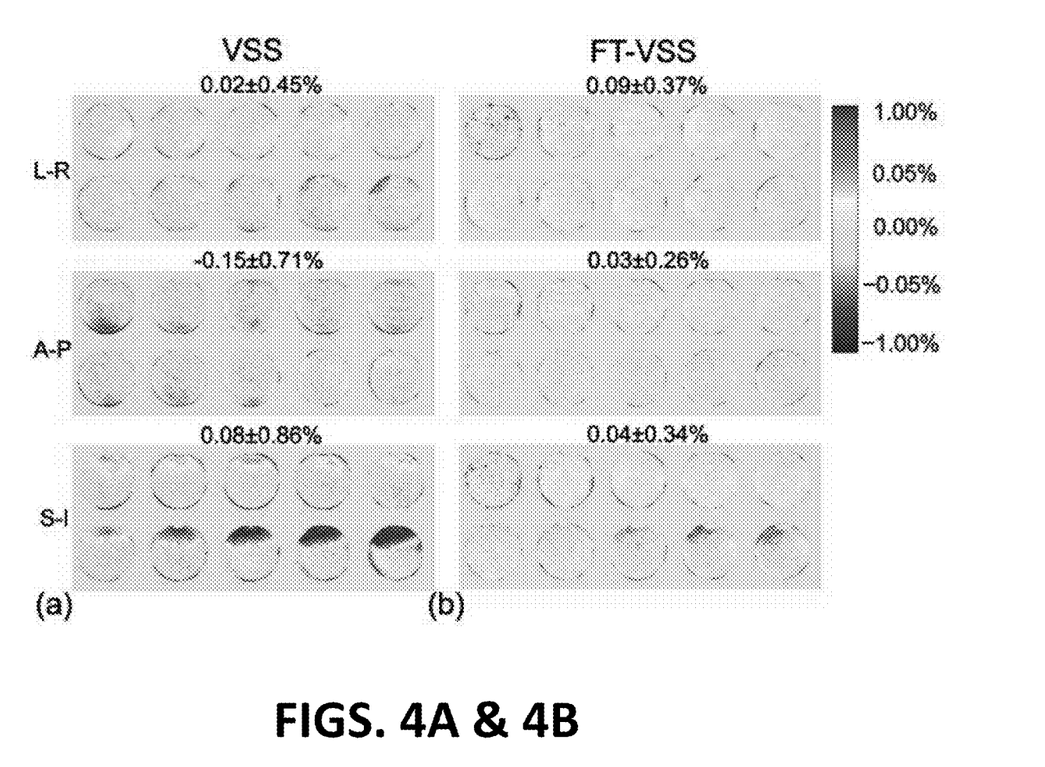

FIGS. 4A and 4B illustrate views of errors in the signal difference caused by gradient imperfections (such as eddy currents) after employing VS control/label modules on a phantom along different orientations (L-R, A-P, S-I) of velocity-encoding gradients. Results for the VSS and FT-VSS pulse trains are shown in the left and right columns (FIGS. 4A and 4B, respectively). Error maps are normalized to $SI_{PD}$ (percentage displayed). All acquired 10 slices are shown with the averaged error percentage (mean±SD) displayed at the top of each row. FT-VSS pulse trains yielded significantly smaller effects of gradient errors both spatially and between different encoding directions. FIGS. 4A and 4B display the effects of gradient imperfections along three orthogonal directions on VSS and FT-VSS label/control modules across 10 continuous slices of the phantom. The normalized subtraction errors (mean±SD) along L-R, A-P and S-I directions are 0.02±0.45%, −0.15±0.71% and 0.08±0.86% for VSS, as illustrated in FIG. 4A, vs. 0.09±0.37%, 0.03±0.26% and 0.04±0.34% for FT-VSS, as illustrated in FIG. 4B, respectively. Compared to conventional VSS, the FT-VSS results showed less variation (SD) both spatially and over different encoding directions, thus more resistance to eddy currents and other gradient imperfections. The improvement is especially apparent for VS gradients along A-P and S-I directions, where both the mean and SD values from FT-VSS pulse trains, as in FIG. 4B, are less than half of those from VSS modules, as in FIG. 4A.

Figure 5:
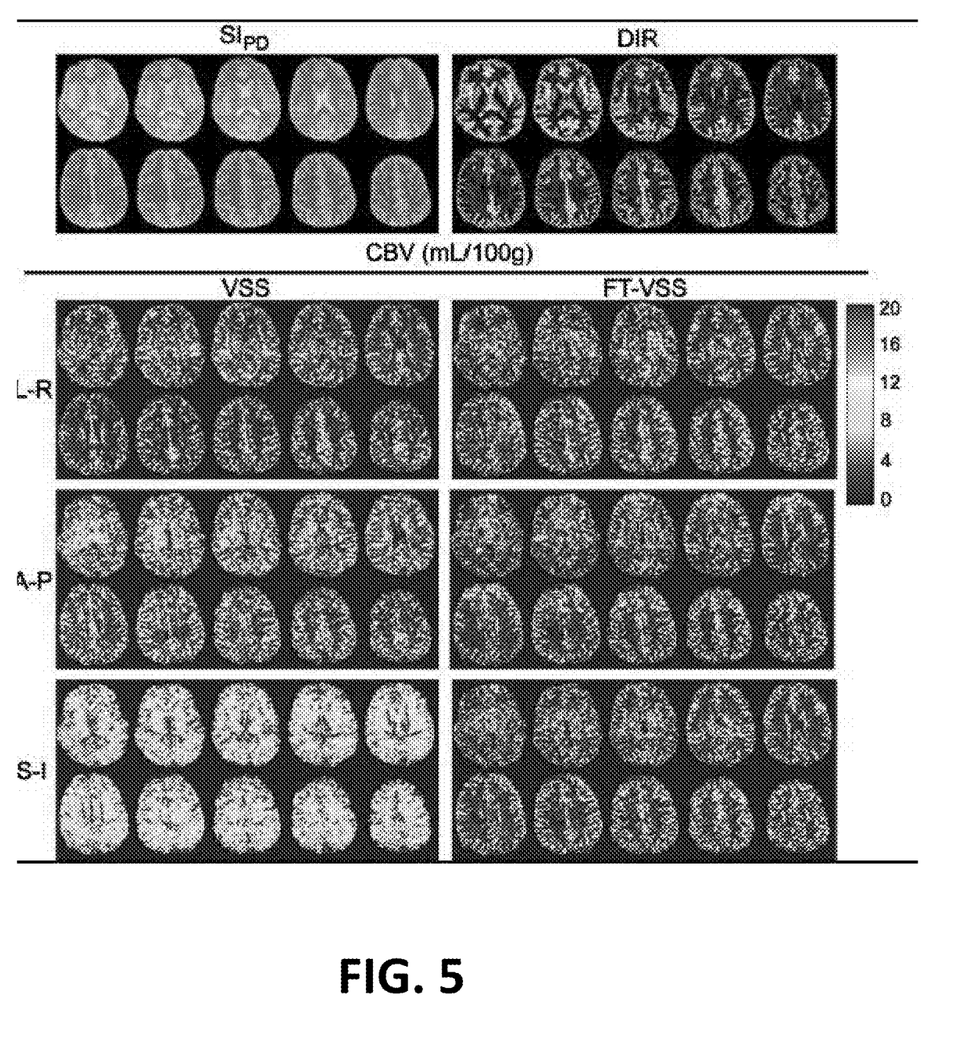
FIG. 5 illustrates representative image views of all 10 slices acquired from subject #5, according to an embodiment of the present invention.

Representative data from all 10 slices for one female subject (#5) are shown in FIG. 5 with $SI_{PD}$, DIR, and CBV maps acquired using VSS and FT-VSS pulse trains. FIG. 5 illustrates representative image views of all 10 slices acquired from subject #5, according to an embodiment of the present invention. The $SI_{PD}$ images, the DIR images for visualizing gray matter only, and CBV maps calculated from experiments using VSS and FT-VSS pulse trains with various velocity-encoding directions. VSS generated some visible gradient-related artifacts in the middle of first four slices for the A-P direction and significant artifacts throughout all slices for S-I direction. FT-VSS produced more consistent CBV contrast across different velocity-encoding directions with significantly reduced artifacts.

Figures 6A, 6B, 6C, 6D:
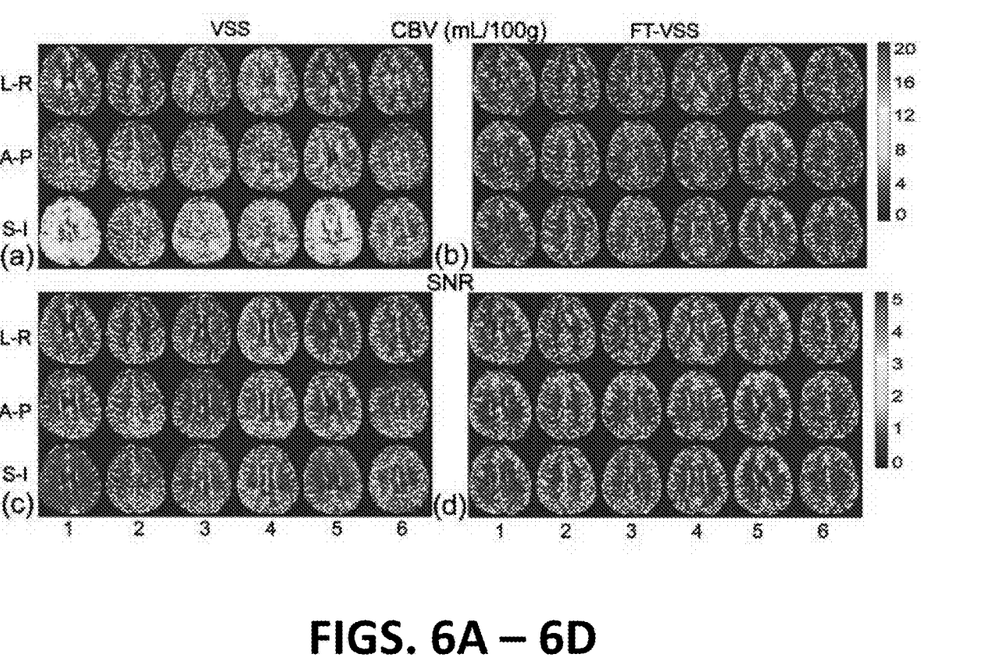
FIGS. 6A-6D show the CBV maps and the corresponding temporal SNR images of the 5$^{th}$ slice obtained using VSS, as illustrated in FIGS. 6A and 6C, and FT-VSS, as illustrated in FIGS. 6B and 6D, in all 6 subjects.

FIGS. 6A-6D show the CBV maps and the corresponding temporal SNR images of the $5^{th}$ slice obtained using VSS, as illustrated in FIGS. 6A and 6C, and FT-VSS, as illustrated in FIGS. 6B and 6D, in all 6 subjects. The VSS results showed noticeable and sometimes substantial artifacts in A-P and S-I directions, illustrated in FIG. 6A, similar to the EC effect observed in the phantom experiments, illustrated in FIGS. 4A and 4B. In contrast, FT-VSS produced CBV maps that were more consistent across all three directions with a higher SNR in GM, as illustrated in FIGS. 6B and 6D.

FIGS. 6A-6D illustrate image views of a comparison of the estimated CBV maps, as illustrated in FIGS. 6A and 6B, and temporal SNR images, as illustrated in FIGS. 6C and 6D on 6 subjects (only the 5th slice of each subject is shown). The images are based on VSS pulse trains, as illustrated in FIGS. 6A and 6C and FT-VSS pulse trains, as illustrated in FIGS. 6B and 6D, with velocity-encoding gradients along L-R, A-P, and S-I directions. CBV quantification employing FT-VSS pulse trains yielded much less artifacts, more consistent CBV contrast, and higher temporal SNR, as illustrated in FIGS. 7A-7D, than for conventional VSS modules.

Figure 7A:
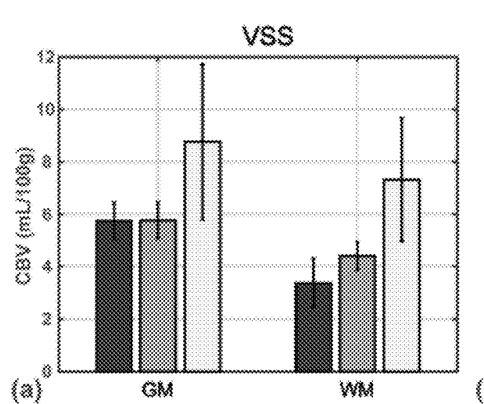
FIGS. 7A-7D illustrate exemplary image views of a comparison of averaged CBV, as illustrated in FIGS. 7A and 7B, and temporal SNR values, as illustrated in FIGS. 7C and 7D, from the GM and WM ROIs of 6 subjects based on VSS pulse trains, as illustrated in FIGS. 7A and 7C, and FT-VSS pulse trains, as illustrated in FIGS. 7B and 7D, with the three orthogonal velocity-encoding directions.
Figure 7B:
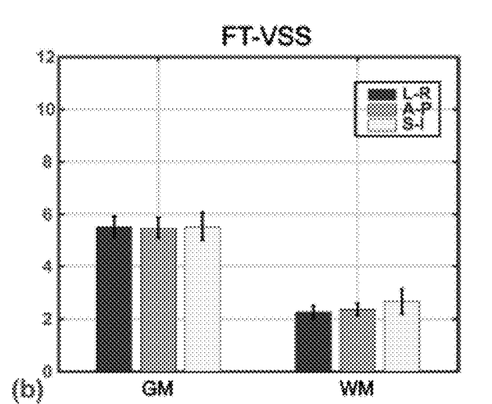
Figure 7C:
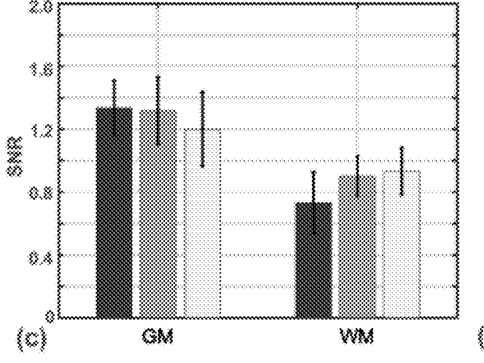
Figure 7D:
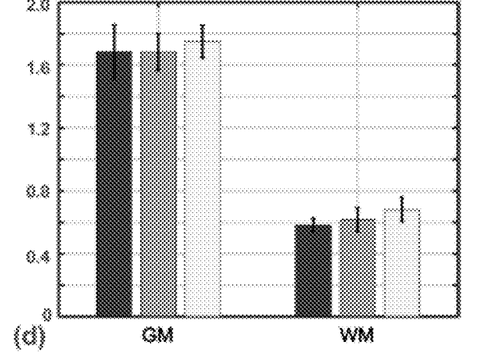

Averaged CBV and SNR values within GM and WM ROIs and their GM/WM ratios are shown in FIGS. 7A-7D and Table 2, below, for VSS and FT-VSS with VS gradients along L-R, A-P and S-I directions, respectively. Compared to the large variations from the conventional VSS methods for different velocity-encoding directions, FT-VSS yielded more consistent mean CBV values: 5.5±0.4, 5.5±0.4 and 5.5±0.5 mL/100 g for GM, and 2.3±0.2, 2.4±0.2 and 2.7±0.5 mL/100 g for WM, as illustrated in FIGS. 7A and 7B and shown in Table 2. Furthermore, the mean temporal SNR values of GM CBV from FT-VSS based scans were 31-50% higher than the ones from VSS based scans, as illustrated in FIGS. 7C and 7D and shown in Table 2. The higher SNR values of WM from VSS methods are attributed to the artifacts related to gradient imperfections.

FIGS. 7A-7D illustrate exemplary image views of a comparison of averaged CBV, as illustrated in FIGS. 7A and 7B, and temporal SNR values, as illustrated in FIGS. 7C and 7D, from the GM and WM ROIs of 6 subjects based on VSS pulse trains, as illustrated in FIGS. 7A and 7C, and FT-VSS pulse trains, as illustrated in FIGS. 7B and 7D, with the three orthogonal velocity-encoding directions. Compared to VSS results, FT-VSS yielded more consistent CBV values among different encoding directions and higher temporal SNR in GM.

TABLE 2

Averaged CBV and temporal SNR values (mean ± SD, n = 6) in GM and WM ROIs and their GM/WM ratios using VSS and FT-VSS pulse trains with velocity-encoding gradients along L-R, A-P, and S-I directions.

|     |     | VSS | | | FT-VSS | | |
| --- | --- | --- | --- | --- | --- | --- | --- |
|     |     | GM  | WM  | ratio | GM | WM | ratio |
| CBV | L-R | 5.8 ± 0.7 | 3.4 ± 0.9 | 1.7 | 5.5 ± 0.4 | 2.3 ± 0.2 | 2.4 |
|     | A-P | 5.8 ± 0.7 | 4.4 ± 0.5 | 1.3 | 5.5 ± 0.4 | 2.4 ± 0.2 | 2.3 |
|     | S-I | 8.8 ± 3.0 | 7.3 ± 2.4 | 1.2 | 5.5 ± 0.5 | 2.7 ± 0.5 | 2.0 |
| SNR | L-R | 1.3 ± 0.2 | 0.7 ± 0.2 | 1.9 | 1.7 ± 0.2 | 0.6 ± 0.0 | 2.8 |
|     | A-P | 1.3 ± 0.2 | 0.9 ± 0.1 | 1.4 | 1.7 ± 0.1 | 0.6 ± 0.1 | 2.8 |
|     | S-I | 1.2 ± 0.2 | 0.9 ± 0.2 | 1.3 | 1.8 ± 0.1 | 0.7 ± 0.1 | 2.6 |

Label and control modules with conventional VSS and the proposed FT-VSS pulse trains were compared in simulations, phantom and in vivo experiments for CBV quantification. Compared to conventional VSS, the FT-VSS based technique demonstrated significantly less susceptibility to gradient imperfections, as illustrated in FIGS. 3A and 3B and 4A and 4B; hence more robust CBV results with higher temporal SNR values across different VS encoding directions were obtained with the advanced FT-VSS methods, as illustrated in FIGS. 5, 6A-6D and 7A-7D. The CBV values derived from FT-VSS based sequences (averaged 5.5 mL/100 g for GM and 2.5 mL/100 g for WM) were comparable to those reported in the literature using other imaging modalities.

For VS pulse trains, sensitivity to eddy currents can be reduced by lengthening the gaps between gradient lobes and the following refocusing pulses, which inevitably increase $T_{VS}$. A prolonged $T_{VS}$ causes stronger $T_2$ based signal losses; thus a compromise has to be made between gradient and $T_2$ effects. Compared to the 40 ms VSS with 4 ms gaps, a 60 ms VSS with 10 ms gaps reduces EC effects substantially (data not shown), but at the cost of signal loss of more than 13% for arterial blood and 31% for venous blood, as illustrated in FIG. 2A. Conversely, the 128 ms FT-VSS with 2.2 ms gaps yielded much better resistance to gradient imperfections, as illustrated in FIGS. 3A and 3B and 4A and 4B, with matched $T_2$ effects for arterial and venous blood signal, as illustrated in FIGS. 2A and 2B.

The better performance of FT-VSS pulse trains over conventional VSS is achieved by more effective background suppression related to their inherent velocity-selective profiles: static tissue signal in the saturation band and flowing spins in the passband, which are opposite from the $M_z$-velocity responses of flow-dephasing VSS pulse trains. Similar to CBF measurements using ASL, it is desirable for the subtraction-based CBV approach to minimize the effects of system fluctuations and physiological noise.

FT-VS S pulse trains enabled more robust CBV measurements and higher SNR compared to the conventional method based on flow-dephasing VSS pulse trains, as demonstrated by numerical simulation, phantom studies and in vivo imaging. The inherent velocity-selective profiles of FT-VSS impart greater immunity to gradient imperfections and simultaneously, superior tissue background suppression. Its clinical value will be further investigated in patients with cerebrovascular diseases.

The present invention provides, as described above, a novel non-contrast-enhanced method for quantifying absolute CBV values using velocity-selective spin labeling approach was developed at 3T. The technical feasibility was demonstrated and the quantified CBV values of gray matter and white matter of healthy subjects were consistent with literature reports. Further optimization of this reported technique is needed to boost the CBV signal, especially from the vessels with very slow flow, e.g. capillary. Furthermore, this technique is not limited to brain perfusion mapping and can be readily extended to measure blood volume in other parts of the body.

It should be noted that the pulse sequences, imaging protocols, described herein can be executed with a program(s) fixed on one or more non-transitory computer readable medium. The non-transitory computer readable medium can be loaded onto a computing device, server, imaging device processor, smartphone, tablet, phablet, or any other suitable device known to or conceivable by one of skill in the art.

It should also be noted that herein the steps of the method described can be carried out using a computer, non-transitory computer readable medium, or alternately a computing device, microprocessor, or other computer type device independent of or incorporated with an imaging or signal collection device. An independent computing device can be networked together with the imaging device either with wires or wirelessly. The computing device for executing the present invention can be a completely unique computer designed especially for the implementation of this method. Indeed, any suitable method of analysis known to or conceivable by one of skill in the art could be used. It should also be noted that while specific equations are detailed herein, variations on these equations can also be derived, and this application includes any such equation known to or conceivable by one of skill in the art.

A non-transitory computer readable medium is understood to mean any article of manufacture that can be read by a computer. Such non-transitory computer readable media includes, but is not limited to, magnetic media, such as a floppy disk, flexible disk, hard disk, reel-to-reel tape, cartridge tape, cassette tape or cards, optical media such as CD-ROM, writable compact disc, magneto-optical media in disc, tape or card form, and paper media, such as punched cards and paper tape.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A method for determining blood volume for a subject comprising:

performing a Fourier-transform velocity-selective saturation (FT-VSS) pulse train with a magnetic resonance imaging scanner, wherein the FT-VSS pulse train is a concatenated series of small-flip-angle RF pulses interleaved with velocity-encoding gradients, and wherein the FT-VSS pulse train is configured for FT-VSS labeling modules to saturate static tissue while preserving spins flowing above a cutoff velocity (Vc), while the FT-VSS labeling modules apply saturation universally on all spins;

embedding refocusing pulses between FT-VSS pulse trains;

cancelling out a signal from static tissue;

performing a pair of acquisitions with the magnetic resonance imaging scanner; and determining the blood volume for the subject from a difference signal that results from a flowing blood compartment above the Vc, after the signal from the static tissue is cancelled out.

2. The method of claim 1 further comprising using refocusing pulses comprising adiabatic pulses or composite pulses.

3. The method of claim 1 further comprising using a velocity-sensitized labeling module comprising ±90° pulses.

4. The method of claim 1 further comprising using alternating velocity-encoding gradients.

5. The method of claim 1 further comprising leaving a gap between a gradient lobe and an RF pulse of the FT-VSS pulse train to minimize the effect of eddy currents.

6. The method of claim 1 further comprising generating a non-contrast-enhanced MRI map of blood volume.

7. The method of claim 1 further comprising using the FT-VSS pulse trains in paired control and label modules for separating vascular signal by subtraction.

8. The method of claim 1 further comprising leveraging a subtraction-based method using the pair of acquisitions immediately following velocity-sensitized pulse trains for a label module and its corresponding control module, respectively.

9. The method of claim 1 further comprising cancelling out a signal of static tissue and a resulting difference signal comes from the flowing blood compartment above a cutoff velocity.

10. The method of claim 1 further comprising normalizing to a proton density-weighted image acquired separately and scaled with blood T1 and T2 relaxation factors and obtaining a quantitative measurement of blood volume.

11. A system for determining blood volume for a subject comprising:
a magnetic resonance imager; and
a non-transitory computer readable medium programmed for:
performing a Fourier-transform velocity-selective saturation (FT-VSS) pulse train with the magnetic resonance imager, wherein the FT-VSS pulse train is a concatenated series of small-flip-angle RF pulses interleaved with velocity-encoding gradients, and wherein the FT-VSS pulse train is configured for FT-VSS labeling modules to saturate static tissue while preserving spins flowing above a cutoff velocity (Vc), while the FT-VSS labeling modules apply saturation universally on all spins;
embedding refocusing pulses between FT-VSS pulse trains;
cancelling out a signal from static tissue;
performing a pair of acquisitions with the magnetic resonance imager; and
determining the blood volume for the subject from a difference signal that results from a flowing blood compartment above the Vc, after the signal from the static tissue is cancelled out.

12. The system of claim 11 further comprising the non-transitory computer readable medium being programmed for using refocusing pulses comprising adiabatic pulses or composite pulses.

13. The system of claim 11 further comprising the non-transitory computer readable medium being programmed for using a velocity-sensitized labeling module comprising ±90° pulses.

14. The system of claim 11 further comprising the non-transitory computer readable medium being programmed for using alternating velocity-encoding gradients.

15. The system of claim 11 further comprising the non-transitory computer readable medium being programmed for leaving a gap between a gradient lobe and an RF pulse of the FT-VSS pulse train to minimize the effect of eddy currents.

16. The system of claim 11 further comprising the non-transitory computer readable medium being programmed for generating a non-contrast-enhanced MRI map of blood volume.

17. The system of claim 11 further comprising the non-transitory computer readable medium being programmed for using the FT-VSS pulse trains in paired control and label modules for separating vascular signal by subtraction.

18. The system of claim 11 further comprising the non-transitory computer readable medium being programmed for leveraging a subtraction-based method using the pair of acquisitions immediately following velocity-sensitized pulse trains for a label module and its corresponding control module, respectively.

19. The system of claim 11 further comprising the non-transitory computer readable medium being programmed for cancelling out a signal of static tissue and a resulting difference signal comes from the flowing blood compartment above a cutoff velocity.

20. The system of claim 11 further comprising the non-transitory computer readable medium being programmed for normalizing to a proton density-weighted image acquired separately and scaled with blood T1 and T2 relaxation factors and obtaining a quantitative measurement of blood volume.

\* \* \* \* \*